United States Patent [19]
Desy

[11] Patent Number: 5,983,390
[45] Date of Patent: Nov. 16, 1999

[54] DISPOSABLE FACE SHIELD

[75] Inventor: Raoul O. Desy, Sturbridge, Mass.

[73] Assignee: Cabot Safety Intermediate Corporation, Newark, Del.

[21] Appl. No.: 08/900,235

[22] Filed: Jul. 24, 1997

[51] Int. Cl.$^6$ ........................................... A61F 9/00
[52] U.S. Cl. ........................................ 2/15; 2/9; 128/858
[58] Field of Search ............................... 2/11, 15, 9, 206, 2/426, 428; 128/863, 858; 24/713.8

[56] References Cited

U.S. PATENT DOCUMENTS

| | | | |
|---|---|---|---|
| 2,342,982 | 12/1944 | Stern et al. | 2/9 |
| 4,755,040 | 7/1988 | Haslbeck | 2/428 |
| 4,793,001 | 12/1988 | Accardi | 2/9 |
| 4,867,178 | 9/1989 | Smith | 2/9 |
| 4,884,296 | 12/1989 | Nix, Jr. | 2/11 |
| 4,935,287 | 6/1990 | Johnson et al. | 428/198 |
| 4,945,574 | 8/1990 | Dagher | 2/206 |
| 5,337,419 | 8/1994 | Russell | 2/206 |
| 5,440,760 | 8/1995 | Highsmith | 2/11 |
| 5,584,078 | 12/1996 | Saboory | 2/427 |

*Primary Examiner*—Diana Oleksa
*Assistant Examiner*—Katherine M. Moran
*Attorney, Agent, or Firm*—Cantor Colburn LLP

[57] ABSTRACT

A disposable face shield having an improved attachment mechanism for securing a band to attach the shield to a user's face is disclosed. The disposable face shield includes a flexible transparent member having opposed slits therethrough. The slits have a length and are disposed on an upper portion of the transparent member. An elastic band having a width greater than the length of the slits is looped through the slits. The slits are arcuate which allows the ends of the band to be removably and adjustably disposed through the slits. A flexible forehead support member is provided on the upper portion of the transparent to nestle against a user's forehead.

15 Claims, 2 Drawing Sheets

DISPOSABLE FACE SHIELD

BACKGROUND OF THE INVENTION

1. Field of the Invention

This invention relates generally to face shields. More particularly, this invention relates to a disposable face shield having an improved adjustable attachment for an elastic band securing the shield to the user's head.

2. Prior Art

It has long been advantageous for individuals working with liquids to wear a protective face shield to prevent those liquids from spattering on the face. For example, face protection in medical procedures to prevent the splattering of blood on the face has become critical in recent years with the occurrence of the deadly AIDS virus and the appearance of other harmful disease producing agents. It is also advantageous in medical procedures to use disposable surgical equipment where possible to substantially reduce the risk of infection and the cost of sterilizing the surgical equipment. Additionally, cleaning face shields of deposited chemicals, such as blood, paint, adhesives, dyes, solvents, resins, etc., is time consuming and often ineffective. Thus, disposable face shields have seen a wide application in various industries, e.g. medicine, dentistry, painting, manufacturing, and the like.

Because of the wide application and use of disposable face shields, the mounting bands or straps which secure the shield to the face must be adjustable to accommodate a variety of different sized faces and heads. Prior art face shields utilize a fastener or integral member to attach the band or strap to the shield. An example of such a prior art shield is found in U.S. Pat. No. 5,113,528. Other face shields incorporate an integral curved brow member to affix the shield to the user's head, such as those found in U.S. Pat. No. 5,008,114 and Des. Patent No. 311,782.

The use of curved brow members is less than ideal as attachment of the shield to the user's head is often uncomfortable and unstable. Other prior art disposable face shields which use elastic bands and/or nonelastic straps are also less than ideal as a fastener or an integral portion of the shield is required to affix the strap to the shield which increases the cost of manufacture.

Thus, the industry is in need of a disposable face shield which provides a reliable and inexpensive adjustable attachment mechanism for securing a band or strap to attach the shield to the face and head.

SUMMARY OF THE INVENTION

The above-discussed and other drawbacks and deficiencies of the prior art are overcome or alleviated by the face shield of the present invention. In accordance with the present invention, a disposable face shield having an improved attachment mechanism for securing a band to attach the shield to a user's face is disclosed. The disposable face shield includes a flexible transparent member having opposed slits therethrough. The slits have a length and are disposed on an upper portion of the transparent member. An elastic band having a width greater than the length of the slits is looped through the slits. The slits are arcuate which allows the ends of the band to be removably and adjustably disposed through the slits. A flexible forehead support member is provided on the upper portion of the transparent member to nestle the shield against a user's forehead.

BRIEF DESCRIPTION OF THE DRAWINGS

Referring to the drawings wherein like elements are numbered alike in the several FIGURES.

DETAILED DESCRIPTION OF THE PREFERRED EMBODIMENT

Figure 1:
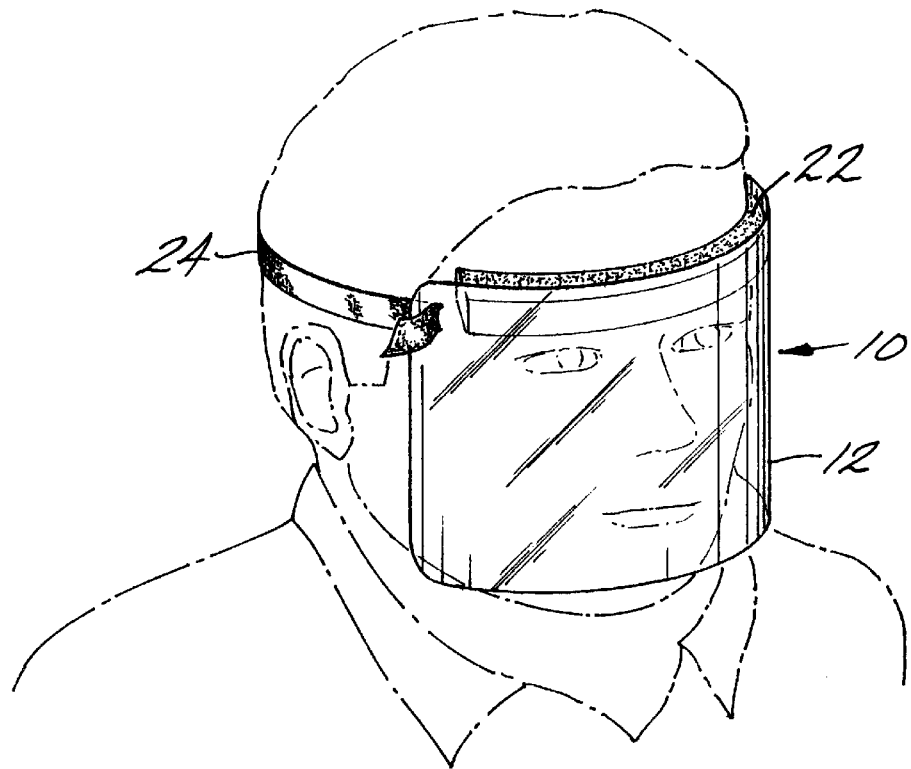
FIG. 1 is a perspective view of a face shield in accordance with the present invention mounted on a user's head.

Referring simultaneously to FIGS. 1 through 6, a disposable face shield in accordance with the present invention is generally shown at 10. Face shield 10 includes a generally rectangular transparent member comprising a plastic film 12 having an upper portion 14, a lower portion 16, and opposed sides, 18 and 20. An elongated flexible forehead support member 22 is disposed at upper portion 14 and nestles against a user's forehead when shield 10 is mounted to a user's face. Shield 10 includes an elastic band 24 having opposed ends 26 and 28. Ends 26 and 28 are adjustably received through respective slits 30 and 32 located on transparent member 12 adjacent sides 18 and 20.

Figure 2:
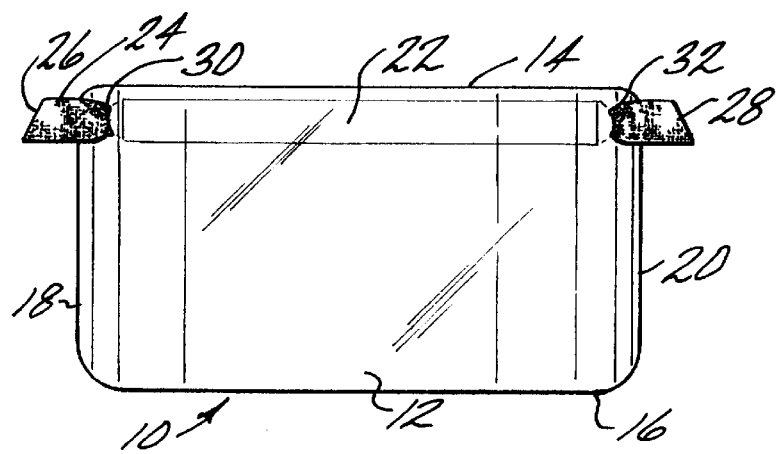
FIG. 2 is a front view of the face shield of FIG. 1.
Figure 5:
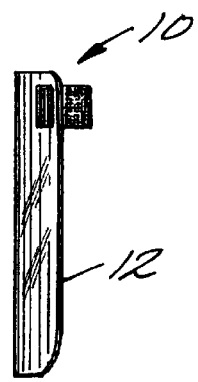
FIG. 5 is a right side view of the face shield of FIG. 1.
Figure 4:
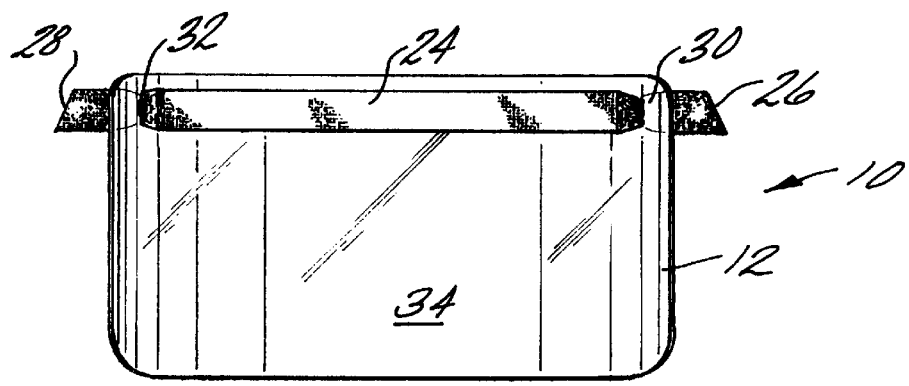
FIG. 4 is a back view of the face shield of FIG. 1.

Referring now to FIGS. 2 and 4, transparent member 12 is a two sided transparent plastic film, such as Kodar PETG copolyester 6763 commercially available from Eastman Plastics (ethylene -1,4-cyclohexylenedimethylene terephthalate (having a second glycol)), and is generally flexible from a flat position to curve about a user's face. Thus, shield 10 may be packaged in the flat position for ease of storage and transportation. Preferably, transparent member or film 12 has an anti-fog coating on its inner side 34 which opposes the user to prevent film 12 from fogging as the user breathes. In the preferred embodiment, forehead support member 22 is an elongated block of foam that includes side 37 which defines a forehead engaging portion that deforms to the contour of a user's forehead and includes side 36 which defines an attachment portion for connecting the forehead support member 22 to the transparent member. Forehead support member 22 is so dimensioned so as to allow for variations in facial structure (e.g. different sizes in noses, chins, foreheads, etc.). Preferably forehead support member 22 extends from a position adjacent end 18 to end 20 and is adhesively connected at its side 36 to transparent member 12 (which may be manufactured with an adhesive already disposed thereon). It will be appreciated that the precise geometric configuration of forehead support member 22 may be varied to practice the invention and that a wide variety of different shapes and cross-sections may be substituted (e.g. circular cross section, rectangular cross section, additional foam members, etc.) so long as shield 10 can be sufficiently anchored to a user's face and/or head. Preferably, forehead support member 22 is commercially available blue ether foam.

Figure 6:
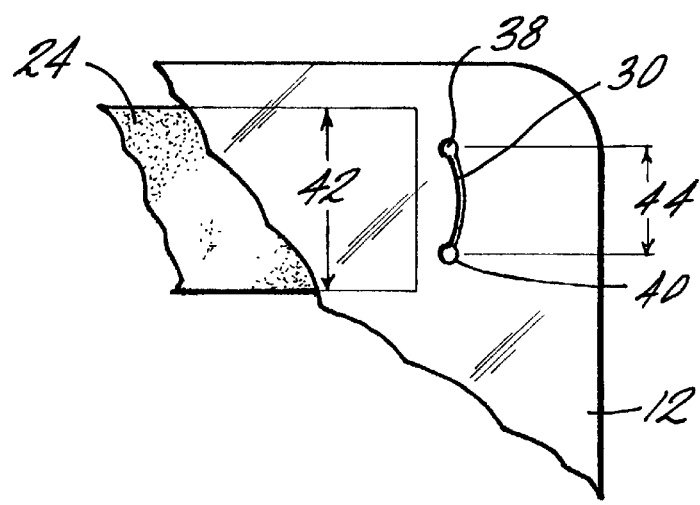
FIG. 6 is a view of an elastic band adjacent a slit in the face shield of FIG. 1 in accordance with the present invention.
Figure 3:
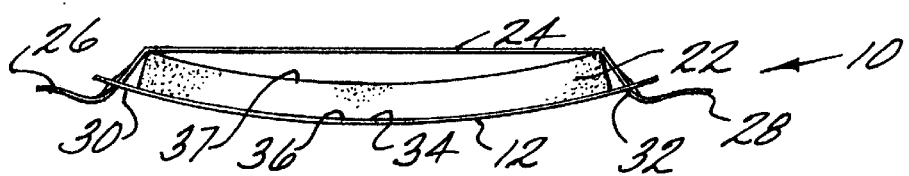
FIG. 3 is a top view of the face shield of FIG. 1.

Referring to FIGS. 2 and 6, slits 30 and 32 are preferably arcuate and include opposed strain relief holes 38 and 40 to prevent stress cracks from occurring in film 12. Slits 30 and 32 are located at upper portion 14 and adjacent respective sides 18 and 20. Slits 30 and 32 are outward of forehead support member 22. It will be appreciated that slit 32 is essentially a mirror image of slit 30. Band 24 is a preferably an elastic band having a width 42 greater than the length 44 of slits 30 and 32. Ends 26 and 28 of band 24 are received through respective slits 30 and 32. The curved or arcuate shape of slits 30 and 32 together with the width of band 24 cause slits 30 and 32 to frictionally engage band 24 to prevent band ends 26 and 28 from exiting respective slits 30 and 32 during use. The curved or arcuate shape of slits 30 and 32 further allows the user to adjust the amount of band 24 disposed through respective slits 30 and 32 by pulling on band 24 at ends 26 and 28 or alternatively between ends 26 and 28 and thereby allow for adjustment of the amount of band 24 between slits 30 and 32 (and the amount of band 24 placed around a user's head). Preferably band 24 is made of a stretch bonded laminate, such as the Stretch Bonded Laminate commercially available from Kimberly Clark. It will be appreciated by those skilled in the art upon reading this disclosure that slits 30 and 32 may be straight and/or vary in size or shape and still removably and adjustably retain band ends 26 and 28.

Thus in use, a user pushes or pulls on band 24 at points between ends 26 and 28 and/or at ends 26 and 28 to adjust the amount of band 24 between slits 30 and 32 available for placement around the head to secure shield 10 to the face so that no other attachment mechanism for band 24 is necessary.

While the preferred embodiments have been shown and described, various modifications and substitutions may be made thereto without departing from the spirit and scope of the present invention. Accordingly, it is to be understood that the present invention has been described by way of illustration and not be limitation.

What is claimed is:

1. A face shield comprising:
   a flexible transparent member having opposed slits formed therethrough, said slits having a length;
   a flexible forehead support member disposed on said transparent member; and
   an elastic band having a first end and an opposing second end and a width greater than said length of said slits so that said first and second ends are frictionally disposed through said slots and adjustably retained therein, wherein at least one of said slots is arcuate in shape.

2. A face shield comprising:
   a flexible transparent member having opposed slits therethrough, said slits having a length, said transparent member further having an upper portion;
   a flexible forehead support member disposed on said upper portion of said transparent member, said forehead support member having a forehead engaging portion adapted to nestle against a forehead; and
   an elastic band having a width greater than said length of said slits, said band further having opposed ends, one of said ends being removably and adjustably disposed through one of said slits, wherein at least one of said slits is arcuate in shape.

3. A face shield according to claim 2, wherein:
   the other of said ends is removably and adjustably disposed through the other of said slits.

4. A face shield according to claim 2, wherein:
   said slits frictionally retain respective said band ends.

5. A face shield according to claim 2, wherein:
   each of said slits include opposed ends, each of said ends including a hole.

6. A face shield according to claim 2, wherein:
   said slits are disposed on said upper portion of said transparent member.

7. A face shield according to claim 2, wherein said forehead support member is disposed between said slits.

8. A face shield according to claim 2, wherein said forehead support member is an elongated piece of foam.

9. A face shield according to claim 2, wherein said transparent member is made of a plastic film.

10. A face shield according to claim 2, wherein said transparent member is a PETG plastic.

11. A face shield according to claim 2, wherein said elastic band is made of a stretch bonded laminate.

12. A face shield according to claim 2, wherein said transparent member includes a side which opposes a user's face, said side having an anti-fog agent disposed thereon.

13. A face shield according to claim 2, wherein said transparent member is rectangular in shape.

14. A face shield according to claim 2, wherein said forehead support member is adhesively connected to said transparent member.

15. A face shield according to claim 2, wherein:
   said transparent member is rectangular shaped and includes opposed top and bottom edges and opposed side edges;
   said forehead support member comprises an elongated block of foam mounted adjacent to and parallel to said top edge; and
   said forehead support member is positioned between said slits.

* * * * *

UNITED STATES PATENT AND TRADEMARK OFFICE
CERTIFICATE OF CORRECTION

PATENT NO. : 5,983,390
DATED : November 16, 1999
INVENTOR(S) : Raoul O. Desy

It is certified that error appears in the above-identified patent and that said Letters Patent is hereby corrected as shown below:

Title Page:
In the Abstract, Line 11 insert --member-- between "transparent" and "to"
In Column 2, Line 63 delete "a" between "is" and "preferably"
In Column 3, Line 27 delete "be" and insert therefor --by--
In Column 3, Line 38 delete "slots" and insert therefor --slits--
In Column 3, Line 39 delete "slots" and insert therefor --slits--

Signed and Sealed this

Thirteenth Day of February, 2001

Attest:

NICHOLAS P. GODICI

*Attesting Officer*   *Acting Director of the United States Patent and Trademark Office*